US00PP18198P3

(12) United States Plant Patent
Oud

(10) Patent No.: US PP18,198 P3
(45) Date of Patent: Nov. 13, 2007

(54) ***LOBELIA* PLANT NAMED 'LOBANTIS'**

(50) Latin Name: *Lobelia erinus*
Varietal Denomination: Lobantis

(75) Inventor: Johannes Simon Nicolaas Oud, Bovenkarspel (NL)

(73) Assignee: Syngenta Seeds B.V., Enkhuizen (NL)

( * ) Notice: Subject to any disclaimer, the term of this patent is extended or adjusted under 35 U.S.C. 154(b) by 1222 days.

(21) Appl. No.: 10/342,894

(22) Filed: Jan. 15, 2003

(65) Prior Publication Data

US 2004/0139519 P1 Jul. 15, 2004

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—Bruce Vrana

(57) ABSTRACT

A new *Lobelia* plant particularly distinguished by its semi-upright mounded plant habit, large flower size and pink flower color.

1 Drawing Sheet

Latin name of the genus and species of the plant claimed: *Lobelia erinus.*
Varietal denomination: 'Lobantis'.

BACKGROUND OF THE NEW PLANT

The present invention comprises a new distinct cultivar of *Lobelia,* botanically known as *Lobelia erinus.* The new cultivar is propagated by cuttings resulting from the cross between 'Y697A' (unpatented) and 'S526' (unpatented). 'Y697A' is a pink flower color selection of our own breeding, having a mounded plant habit and early flowering. 'S526' is a light pink flower color selection of our own breeding, having a strong growth and good branching.

As a result of this cross, the present cultivar was created in 1999 in Enkhuizen, Netherlands and has been repeatably asexually reproduced by cuttings in Enkhuizen, Netherlands over a three-year period. It has been found to retain its distinctive characteristics through successive propagations, and this novelty appears to be firmly fixed.

DESCRIPTION OF THE DRAWING

This new *Lobelia* plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new *Lobelia* plant. The data which defines these characteristics were collected from asexual reproductions carried out in Enkhuizen, Netherlands. The plant history was taken on 12 weeks old plants. Color references are primarily to The R.H.S. Colour Chart of The Royal Horticultural Society of London.

Comparison between the new cultivar 'Lobantis' and a similar cultivar

| | 'Lobantis' | 'Blue Star' (unpatented) |
|---|---|---|
| Plant height | 15 cm | 10 cm |
| Plant width | 30 cm | 35 cm |
| Plant shape | Semi-upright | Spreading |
| Flower Color | | |
| Upper surface | 76B | 95B |
| Lower surface | 76B | 100A |
| Flower tube | 82C | 95C |

The plant:
*Classification.*—Botanical: *Lobelia erinus.*
Parentage:
*Female parent.*—A seedling named 'Y697A' is one of our seedings from our Y-generation of plants bred in 1998.
*Pollen parent.*—A seedling named 'S526' is one of our seedlings from our S-generation of plants bred in 1992.
Plant description:
*Growth habit.*—Semi-upright, mounded.
*Plant height.*—15 cm.
*Speading area of plant.*—30 cm.
*Growth rate.*—Moderate growth.
*Strength.*—Good.
*Branching character.*—Freely branching and lateral branching at every node. Pinching will enhance branching. Branches strong and flexible.
*Blooming period.*—From May until October.
The stem:
*Diameter.*—1.5 mm.
*Texture.*—Smooth, slightly pubescent, glossy.
*Color.*—RHS 138B.
*Length of internode.*—13 mm, depending on the light conditions where the plant is propagated.
*Shape.*—(Tri)angular.

The foliage:

*Shape.*—Leaves simple, generally symmetrical and flat. Broadly ovate with rounded apex, obtuse to attenuate base and crenate margin.

*Texture.*—Slightly pubescent, glossy.

*Length.*—Young 30 mm, fully expanded 55 mm.

*Width.*—Young 10 mm, fully expanded 23 mm.

*Color.*—Upper side: RHS 137A. Lower side: RHS 138A.

The flower:

*Type and habit.*—Flowers form at apical axis, usually one flower per axil. Flowers labiate, upper lip consisting of two small petals and lower lip consisting of three larger and broader petals. Petals are fused at base into a tube. Freely and continuously flowering. Flowers face outward. Flower persistent. Texture, slightly pubescent. Oblong shape with acute apex and entire margin.

*Flower.*—Width: Upper petals 1 mm, lower petals 6 mm. Length: Upper petals 5 mm, lower petals 10 mm. Depth: 7 mm.

*Texture.*—Smooth, pubescent.

*Buds.*—Length: 7 mm. Diameter: 2 mm. Form: Tubular. Color: Light green.

*Flower color.*—Upper surface: RHS 76B. Lower surface: RHS 76B. Flower tube: RHS 82C.

*Sepals.*—No. of sepals: 5. Length: 6 mm. Width: 0.5 mm. Texture: Smooth, slightly pubescent. Color: RHS 137B.

*Flower stem.*—Length: 25 mm. Angle: Upright. Strength: Rigid, flexible. Color: RHS 137B.

*Flower throat.*—Color: Upper RHS 76B. Lower RHS 76B, spots RHS N81A. Texture: Whiskered.

Reproductive organs:

*Androecium.*—Stamen number: 5. Anther shape: Oblong. Anther length: 1 mm. Pollen color: RHS 202B. Amount of pollen: Moderate.

*Gynoecium.*—Pistil length: 8 mm. Stigma shape: Bilobate. Stigma diameter: 1 mm. Stigma color: N87A. Style color: Light green. Ovary color: RHS 137B.

Seed development: No seed development has been observed on plants of the new *Lobelia.*

Disease resistance: No susceptibility or resistance to fungal, bacterial or viral pathogens has been noted.

What is claimed is:

1. A new and distinct variety of *Lobelia* plant, substantially as illustrated and described herein.

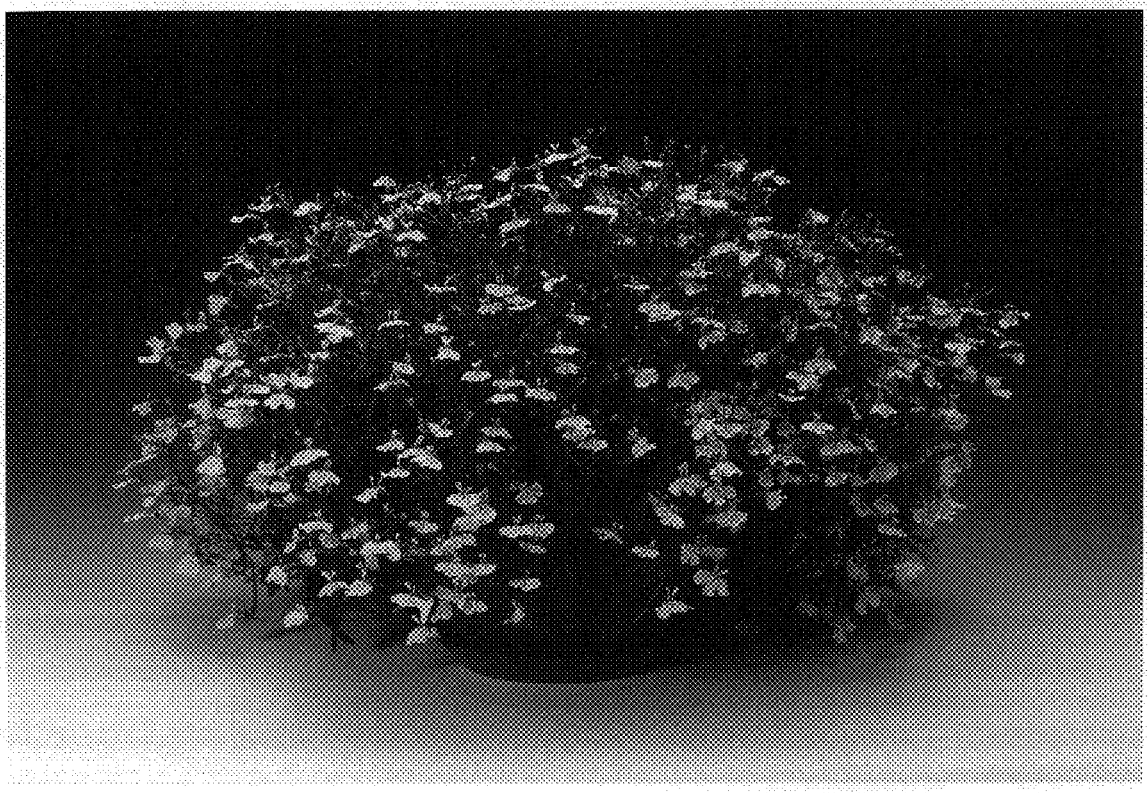

* * * * *